(12) United States Patent
Semisynov

(10) Patent No.: US 10,874,535 B2
(45) Date of Patent: Dec. 29, 2020

(54) DEVICE AND METHOD FOR A SAFE POSITIONING OF A CORONARY STENT IN CORONARY ARTERIES

(71) Applicant: OBSCHESTVO S OGRANICHENNOI OTVETSTVENNOSTJU "SEVEN SANS", Moscow (RU)

(72) Inventor: Ilia Vladimirovich Semisynov, Moscow (RU)

(73) Assignee: SEVEN SONS LTD., Tel-Aviv (IL)

( * ) Notice: Subject to any disclaimer, the term of this patent is extended or adjusted under 35 U.S.C. 154(b) by 318 days.

(21) Appl. No.: 15/761,882

(22) PCT Filed: Dec. 29, 2015

(86) PCT No.: PCT/RU2015/000952
§ 371 (c)(1),
(2) Date: Mar. 21, 2018

(87) PCT Pub. No.: WO2017/052414
PCT Pub. Date: Mar. 30, 2017

(65) Prior Publication Data
US 2018/0280170 A1    Oct. 4, 2018

(30) Foreign Application Priority Data

Sep. 24, 2015 (RU) ................................ 2015140675

(51) Int. Cl.
*A61F 2/95* (2013.01)
*A61F 2/82* (2013.01)
*A61M 25/01* (2006.01)

(52) U.S. Cl.
CPC .............. *A61F 2/95* (2013.01); *A61F 2/9517* (2020.05); *A61F 2002/821* (2013.01); *A61M 25/0136* (2013.01); *A61M 2205/0238* (2013.01)

(58) Field of Classification Search
CPC .. A61F 2/95; A61F 2/958; A61F 2/962; A61F 2002/9517; A61M 25/0136
See application file for complete search history.

(56) References Cited

U.S. PATENT DOCUMENTS 6,293,964 B1    9/2001  Yadav
9,119,716 B2 *  9/2015  Lee ........................ A61F 2/2433
(Continued)

OTHER PUBLICATIONS

CN 101677850 A _ English Abstract.
RU 94453 U1 _ English Abstract.
RU 2012 117 529 A _ English Abstract.

*Primary Examiner* — Sarah W Aleman
(74) *Attorney, Agent, or Firm* — Ladas & Parry LLP

(57) ABSTRACT

The invention is suitable for use in medicine for maximally precise, safe and quick positioning a coronary stent in case of simple and complicated anatomical lesions of the coronary bed as well as for stenting renal, visceral arteries. The claimed device comprise a body with a tail portion, a screw rotation wheel, a screw, a slider with a cam, a bush with clip and a rubber coupling provided thereon, a wedge comprised of two members, a spring and a lock button arranged in the body. In preparation to use the device, the coronary stent on the delivery system is first successively introduced into the device whereafter the coronary stent on the delivery system is manually advanced to the affected area of the coronary artery, the delivery system is locked in the device and the stent is positioned within the coronary artery by means of the rotation wheel.

7 Claims, 15 Drawing Sheets

(56) References Cited

U.S. PATENT DOCUMENTS

Figure 1:
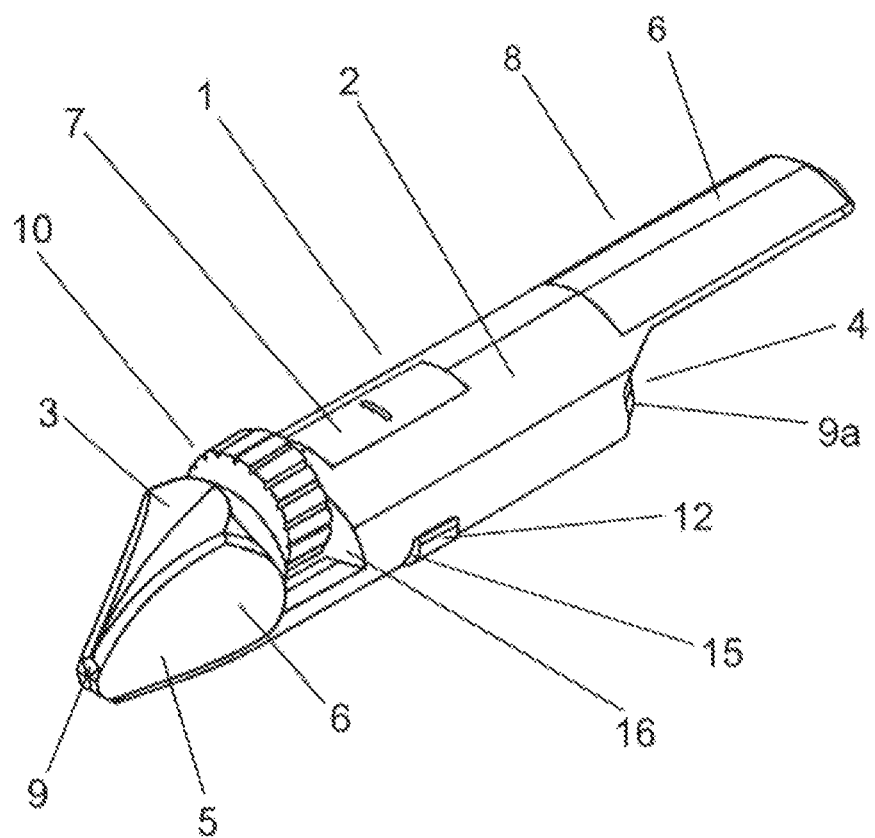

| | | | | |
|---|---|---|---|---|
| 2003/0074045 A1* | 4/2003 | Buzzard | ............ | A61F 2/95 |
| | | | | 623/1.11 |
| 2005/0060016 A1* | 3/2005 | Wu | ............ | A61F 2/95 |
| | | | | 623/1.11 |
| 2010/0191326 A1* | 7/2010 | Alkhatib | ............ | A61F 2/2439 |
| | | | | 623/2.11 |
| 2012/0123528 A1* | 5/2012 | Knippel | ............ | A61F 2/2436 |
| | | | | 623/2.11 |

* cited by examiner

DEVICE AND METHOD FOR A SAFE POSITIONING OF A CORONARY STENT IN CORONARY ARTERIES

RELATED APPLICATION INFORMATION

This application is a 371 of International Application PCT/RU2015/000952 filed 29 Dec. 2015, which claims priority from RU 2015140675 filed 24 Sep. 2015, the contents of which are incorporated herein by reference.

The present invention is suitable for use in medicine for maximally precise, safe and quick positioning a coronary stent in case of simple and complicated anatomical lesions of the coronary bed, in particular within a coronary artery in case of endovascular coronary stenting to recanalize the artery portions constricted due to a lesion.

The device is suitable for use in case of ostial lesions of coronary arteries, bifurcation lesions of coronary arteries including, but not limited to, lesions of left coronary artery trunk and ostial lesions of right coronary artery as well as in case of "stent in stent" implantation for reducing the "overlapped" area.

The use of this device enables the radiation exposure of patients and medical staff as well as exposure of patients to radiopaque medium to be substantially reduced.

The device may be easily used by young professionals in process of their training in the field of interventional cardiology.

In addition, the claimed device may also be used for stenting renal, visceral arteries in a similar way.

A number of devices for positioning a stent within a coronary artery are commercially available.

In particular, known is the OSTIAL PRO stent positioning system available from Merit Medica, USA (U.S. Pat. No. 6,293,964). This patent discloses a device comprising a cone comprised of four flaps, which is in inserted into a guiding catheter together with the coronary stent. The guiding catheter is selectively positioned at the ostium of a coronary artery. The coronary stent is advanced through the guiding catheter to a site located more distally than the coronary artery ostium whereafter the guiding catheter is withdrawn from the artery ostium and from the device. Upon withdrawal from the catheter, the flaps expand to abut against the aortal wall so that the guiding catheter tip cannot be selectively positioned at the coronary artery ostium which is required when stenting the ostium of the trunks of both left and right coronary arteries. All further procedure of positioning the coronary stent at the affected area is accomplished manually.

A disadvantage of the prior art device is it limited application, in particular only in case of ostial lesions of the trunks of left and right coronary arteries, as well as manual positioning of the coronary stent. The claimed device is distinguished primarily by:

quicker and more precise positioning the coronary stent within the coronary artery;
 positioning the stent mechanically rather than manually;
 reduced radiation exposure of patients and medical staff due to a shorter positioning time of the coronary stent;
 applicability of the device in case of lesions of any coronary bed segment;
 reduced exposure of patients to radiopaque medium due to a shorter positioning time of the coronary stent;
 single-use application;
 convenient configuration of the device as an extension the surgeon's hand;
 minimum weight and dimensional characteristics;
 ease of use;
 cost efficient production.

The device is industrially applicable.

The claimed device is a basic modification and comprises a body with a tail portion and wheels arranged in the body a screw rotation wheel, a screw, a slider having a cam, a bush with clips and a rubber coupling arranged thereon, a wedge comprised of two members, a spring and a lock button.

The body having a cylindrical shape is made by casting of medical-grade plastic provided with a moisture-resistant coating where it contacts the operator's hand, wherein the body's left and right halves are integrally formed by casting and joined together after assembly of the mechanism. In the upper body portion, the body is provided with a wheel for rotating a screw, said wheel arranged in a hole for the screw rotation wheel, and a lock button arranged in a lateral hole in the body. In the front body portion having a truncated shape adapted for being held by the operator's left hand thumb and forefinger, recesses are provided allowing the operator to lock the device at a desired position, wherein the left hand thumb recess also serves as a site for locking a coronary guide. and the upper body portion is arranged as a tail-shaped portion for providing a palm rest for the right hand. In the upper body portion, a rectangular window is formed of a transparent material for a control bar with millimetric score marks for positioning and controlling the position of the mechanism for locking the coronary stent delivery system inside the device. A maximum displacement distance of the mechanism for locking the coronary stent delivery system in either direction is limited by the bar size in accordance with the device size. In the body front and rear portions, holes are provided for introducing the coronary stent delivery system inside the body.

Between the truncated portion and the cylindrical portion of the body, there is arranged a screw rotation wheel whose upper portion projects over the body and a lower portion is arranged inside the body and which is rigidly connected to a horizontal screw having a slider arranged thereon slidably along the screw and a cam moveably arranged on the screw spherical member horizontally to the screw with the clips provided on the axis of said cam, said clips being rubber-coated where they contact the delivery system and compressible by a rubber coupling, and on the opposite side of the slider, a wedge is provided comprised of a lateral member and a cone-shaped member, and a spring contacting the lateral member end by means of a lateral through hole in the slider and fixed to the slider wall on the side opposite to the button.

The lateral wedge member is arranged within the lateral hole in the slider on the lock button side and comprises a rectangle with a rounded lateral surface on the lock button side with a through hole provided therein, said hole formed by a cutoff at an angle of 45 degrees on one side and a cutoff at an angle of 90 degrees on the other side and adapted for accommodating end-to-end therein the cone-shaped member whose lower portion is cut off at an angle of 45 degrees, respectively, and the upper portion comprises a cone projecting from the hole in the slider on the hoes side and contacting the clips. Both wedge members are provided with holes through which the coronary stent delivery system advances while in operating state. In the lateral portion of the slider on the side opposite to the lock button, there is provided a spring contacting the surface of the lateral wedge member.

Such arrangement enables a rigid fixation of the coronary stent delivery system as the stent advances both back and forth and at the same time allows the stent to turn freely around its axis.

In the lateral body portion, there is provided a lock button whose inner side arranged inside the body comprises a rectangular plate. The lock button is centered by two lateral stiffening ribs arranged inside the body so that it may freely move towards the wedge and away from the same. The button is arranged such that when depressed, its inner surface exerts pressure on the rounded surface of the lateral wedge member which in turn exerts pressure on the cone-shaped member causing the clips pressed together by the rubber coupling to unlock so that the coronary stent delivery system becomes unlocked. At the same time, the end surface of the lateral wedge member on the spring side enters the through hole in the slider to press on the spring arranged in the slider track.

To return the lock mechanism to the initial position with the locked clips, the button is released so that the spring expands to push the lateral wedge member back to the initial position, and the latter in turn, respectively, brings the button back to the initial position. At the same time, the cone-shaped member also returns to its initial position under the pressure of the clips which in turn contract under the impact of the rubber coupling thereby locking the coronary stent delivery system inside the device.

Therefore, when the button is in a free not depressed position under pressure exerted by the rubber coupling on the clips, the stent delivery system is in a locked position, and when the button is depressed, pressure is exerted on the wedge which causes the clips to unlock so that the coronary stent delivery system becomes unlocked and may freely move along the axis.

In preparation to use the device, the operator depresses the lock button to introduce the coronary stent on the delivery system into the device so that the inner rectangular portion of the button exerts pressure on the wedge which cause the clips pressed together by the rubber coupling to unlock and the coronary stent delivery system is accommodated via through holes provided in the body. When the lock button is no longer depressed, the spring pushes out the lateral wedge member bringing thereby the cone-shaped member and the button to the initial position, the rubber coupling again presses the clips together and locks the delivery system. The operator manually advances the coronary stent on the delivery system accommodated within the device to the affected area of the coronary artery. Then, the lock button is again depressed, the clips unlock and the operator approaches the device to a distance required for holding the same with the left hand fingers, releases the lock button and rotates the screw rotation wheel with his/her right hand thereby translating the rotational movement of the wheel into the linear motion of the slider and advancing the delivery system to a distance required for positioning the coronary stent inside the vessel. By depressing the button, the operator may also bring the mechanism locking the coronary stent delivery system back to the initial position by rotating the wheel in the required direction so that the coronary stent may be further positioned back and forth within the bar size range in each directions.

In an embodiment, the device may be provided with the delivery system locked in advance therein. In this case, there is no step of introducing in advance the coronary stent on the delivery system into the device. The coronary stent on the delivery system is manually advanced to the affected area of the coronary artery and then the lock button is depressed, the clips unlock and the operator approaches the device to a distance required for holding the same with the left hand fingers, releases the lock button and rotates the screw rotation wheel with his/her right hand thereby advancing the delivery system to a distance required for positioning the coronary stent inside the vessel. By depressing the button, the operator may also bring the mechanism locking the coronary stent delivery system back to the initial position by rotating the wheel in the required direction so that the coronary stent may be further positioned back and forth within the bar size range in each direction.

In an embodiment, the stent may be placed on the delivery system in a safe manner using a hollow tube arranged in advance inside the device such that the delivery system with the stent is introduced into the tube which is then removed from the device.

In an embodiment, the device may be provided with a moveable tail portion with a cutout arranged in its front part such that when displaced to an extreme forward position, the control bar may be seen under the same. The tail portion is lockable by means of lateral locks arranged on its sides in the front part thereof and is moveable horizontally along the body on the lateral cutouts. This arrangement allows the operator to select the length of the tail portion so as to adapt the device to the operator's hand and to set the most comfortable palm position when handling the device and also to reduce the dimensions of the device during storage.

As a mechanism of linear motion, other types of gearing may be used, in particular worm gearing, toothed gearing and rope transmission.

Below is provided a list of the attached drawings.

Figure 2:
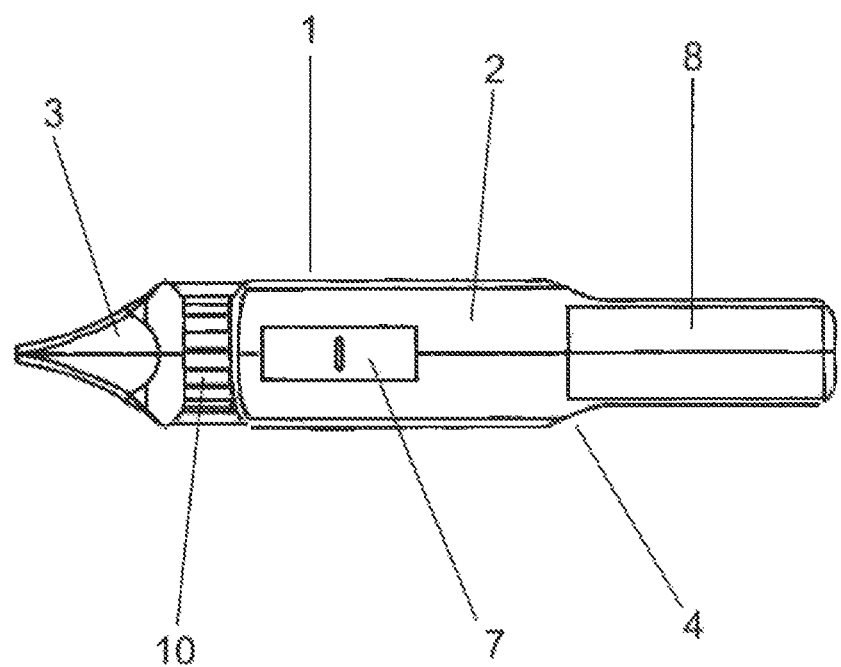
Figure 3:
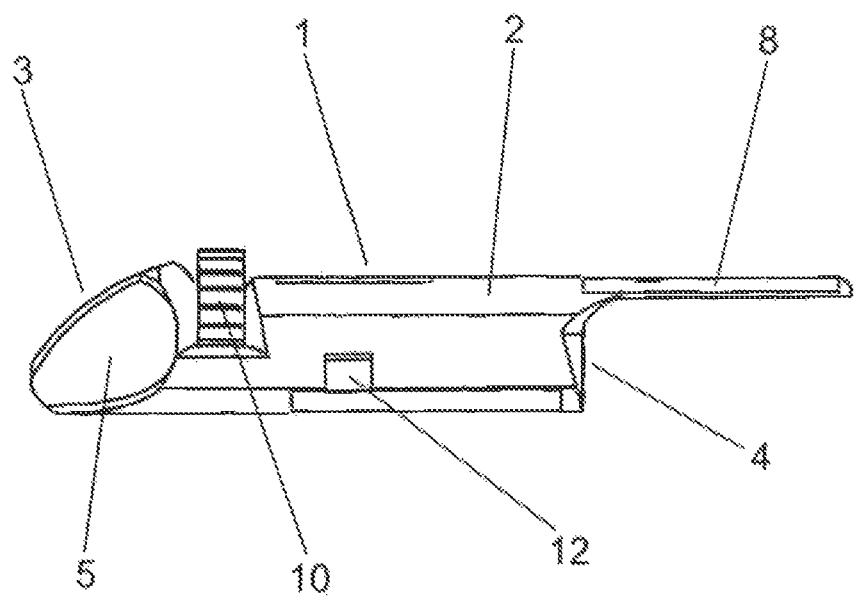
Figure 4:
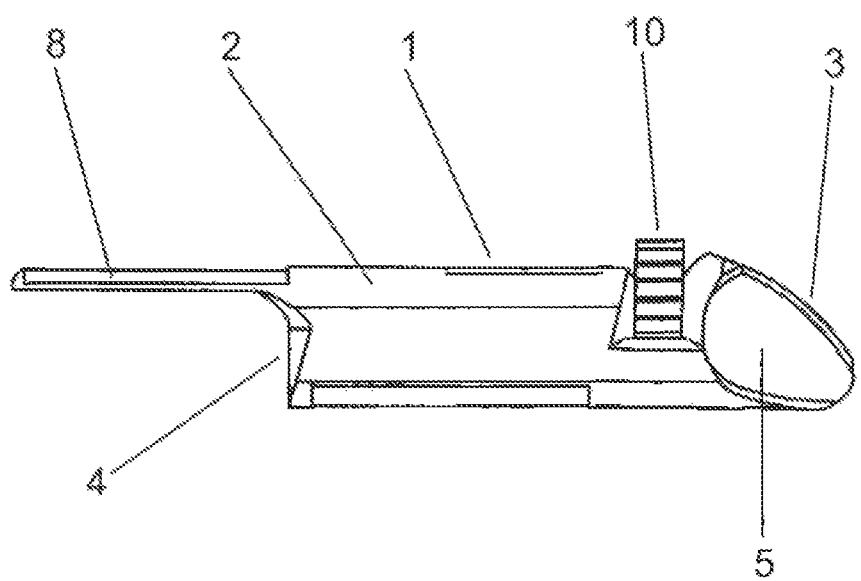
Figure 5:
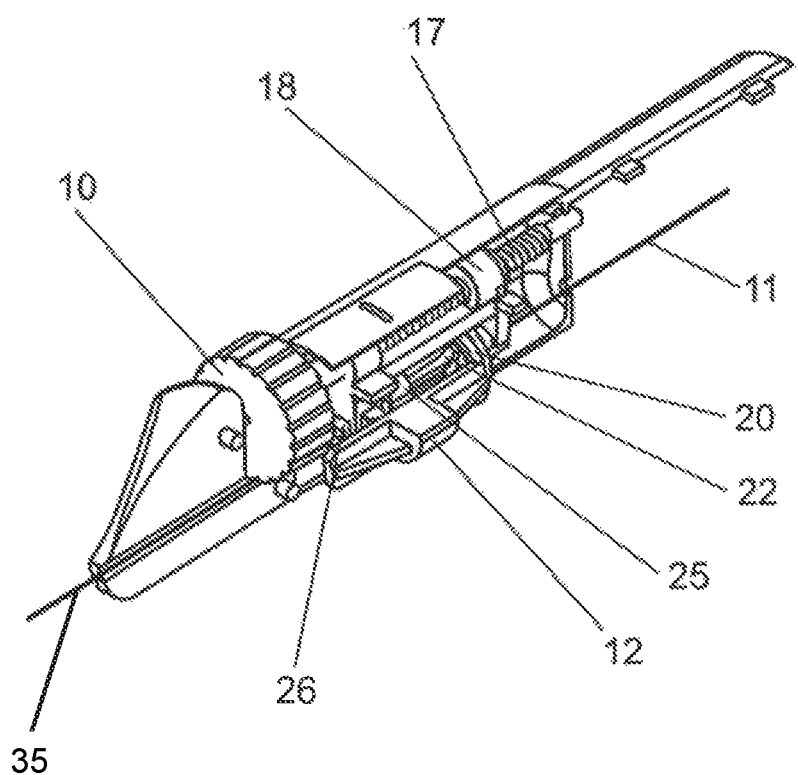
Figure 6:
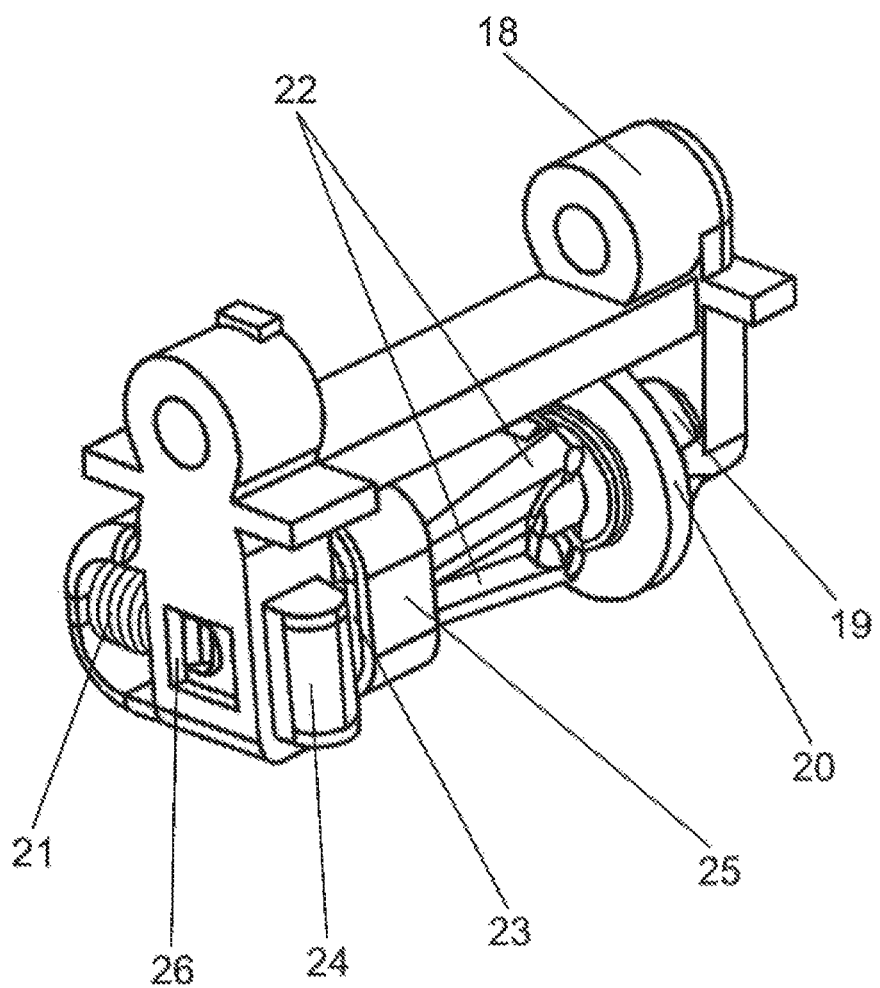
Figure 6A:
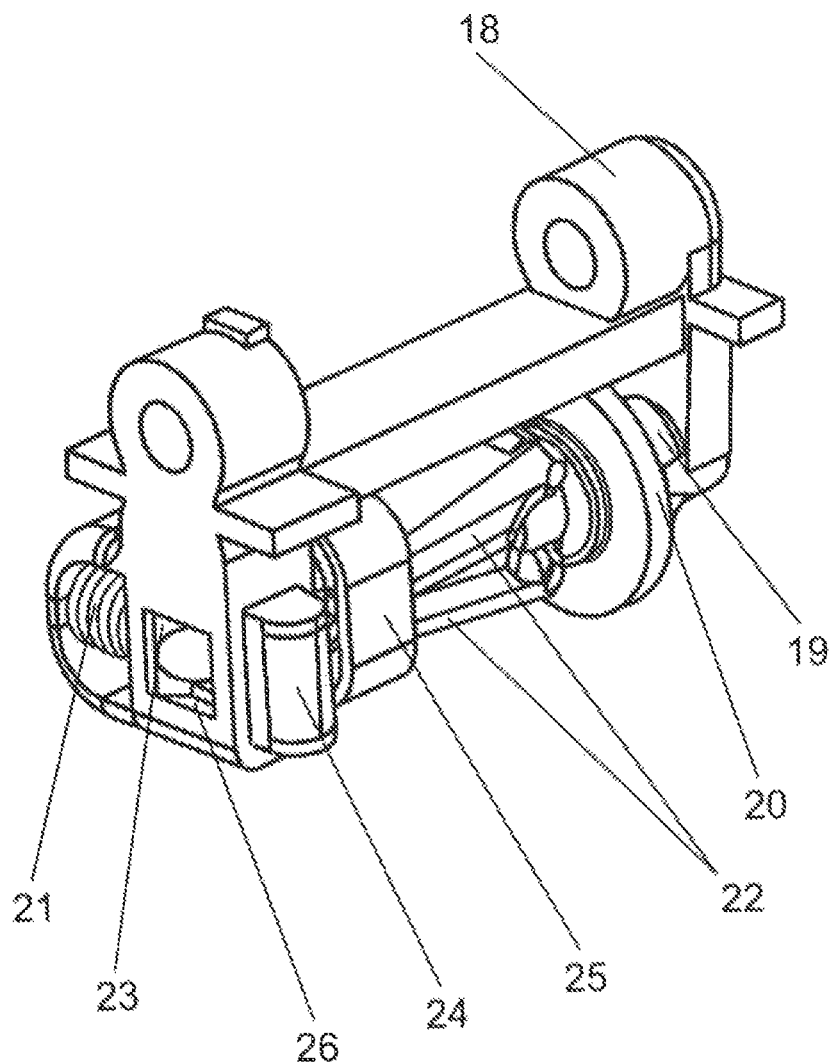
Figure 7:
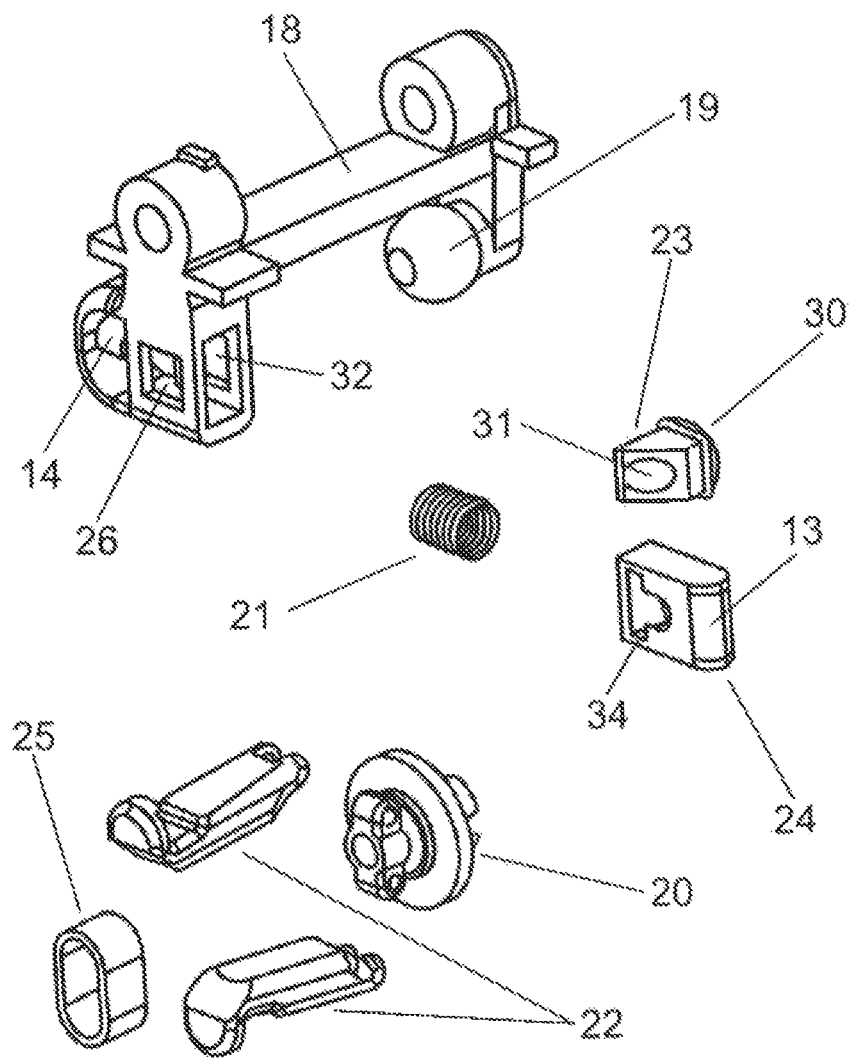
Figure 7A:
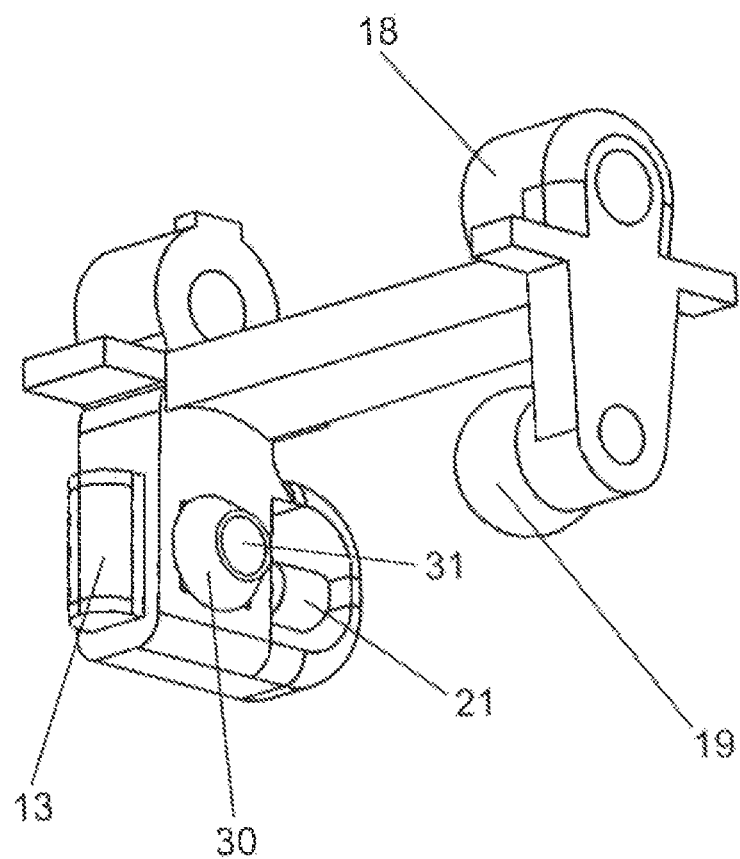
Figure 7B:
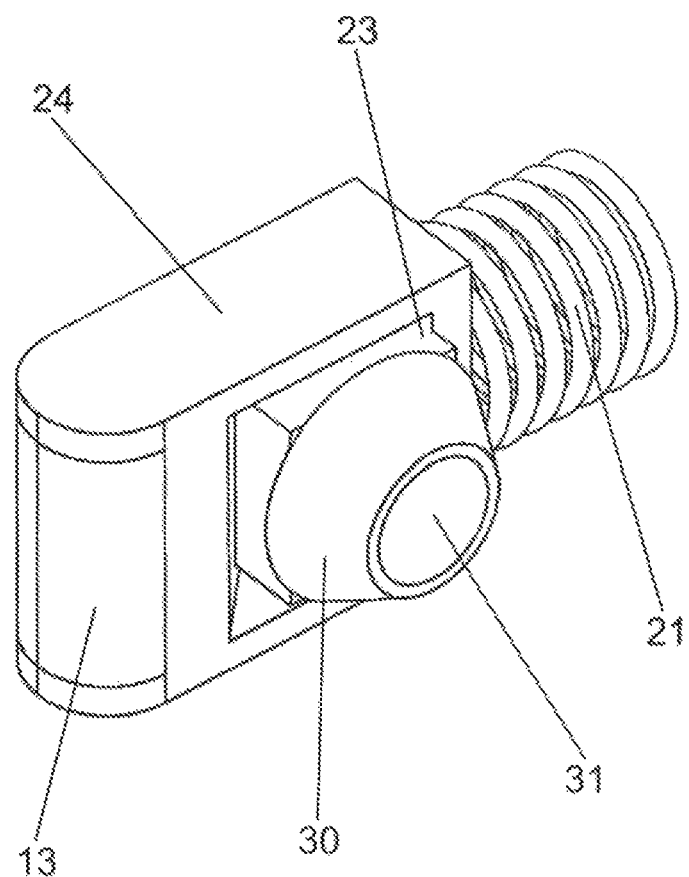
Figure 8:
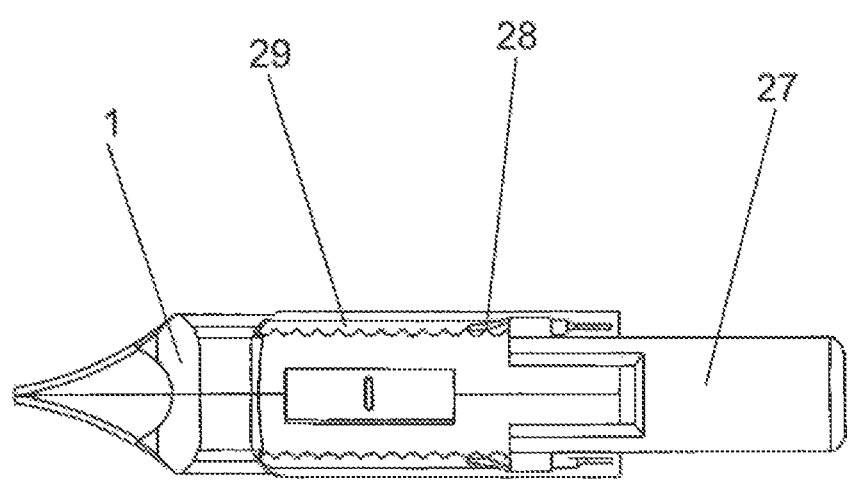
Figure 8A:
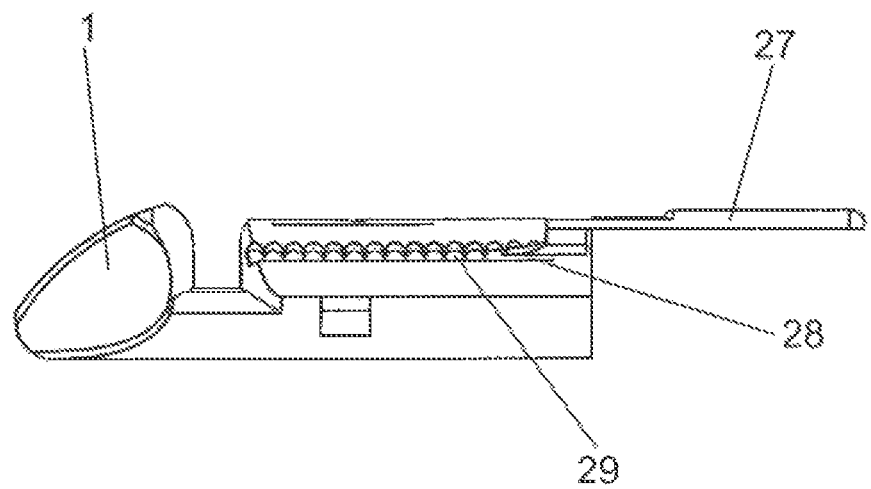
Figure 9:
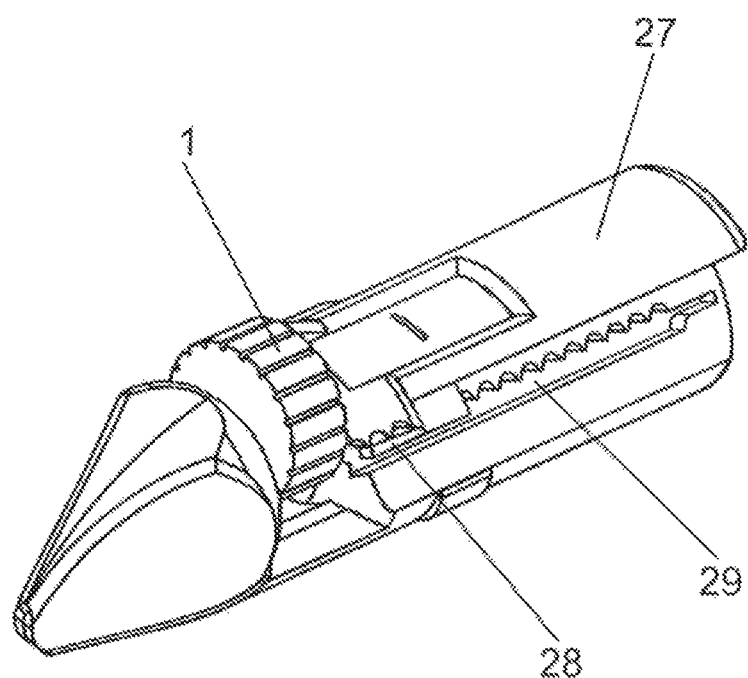
Figure 10:
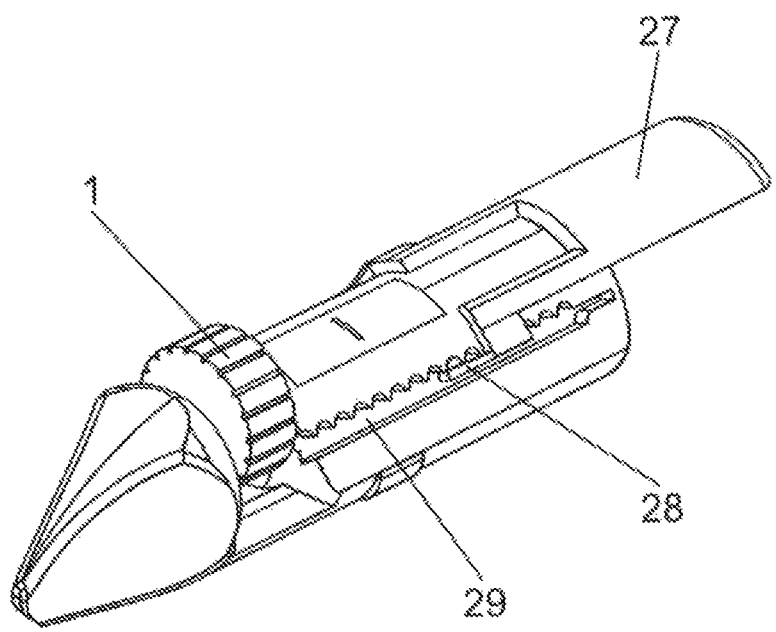
Figure 11:
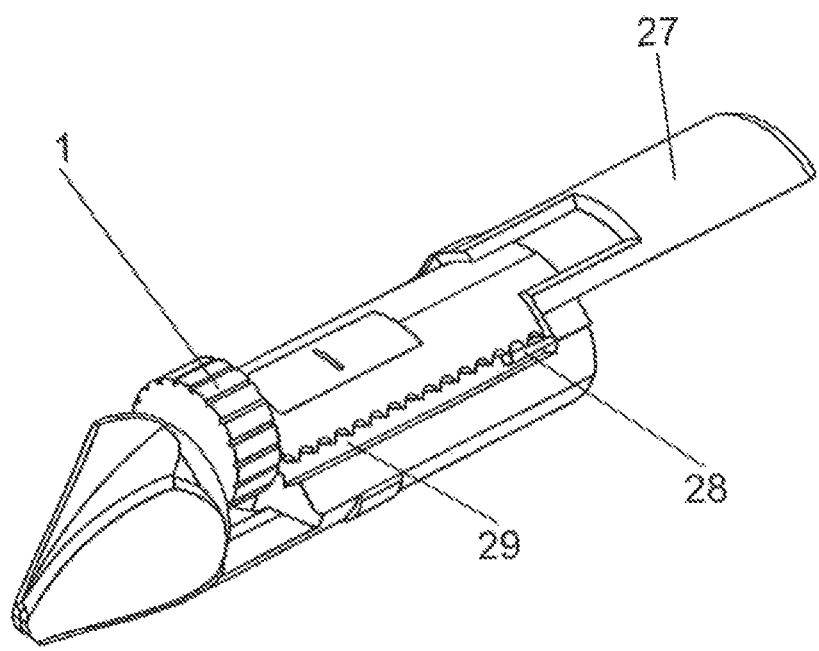

FIG. 1 is a general view of the device showing:
1—device body,
2—cylindrical body portion,
3—truncated front body portion,
4—rounded rear body portion,
5—left hand finger recess,
6—moisture-resistant rubber coating,
7—transparent window for control bar with score marks,
8—palm rest for right hand in the form of tail portion,
9, 9a—through holes in the body for accommodating the delivery system,
10—screw rotation wheel,
12—lock button,
15—lock button hole in the body,
16—screw rotation wheel hole in the body, FIG. 2 is a top view showing:
1—device body
2—cylindrical body portion,
3—front truncated body portion,
4—rounded rear body portion,
7—transparent window for control bar with score marks,
8 —palm rest for right hand in the form of tail portion,
10—screw rotation wheel, FIG. 3 is left side view of the lock button, showing:
1—device body,
2—cylindrical body portion,
3—front truncated body portion,
4—rounded rear body portion,
5—left hand finger recess,
8—palm rest for right hand in the form of tail portion,
10—screw rotation wheel,
12—lock button;

FIG. 4 is a right side view showing:
1—device body
2—cylindrical body portion,
3—front truncated body portion, 4—rounded rear body portion,
5—left hand finger recess,
8—palm rest for right hand in the form of tail portion,
10—screw rotation wheel;
FIG. 5 is a general sectional view of the device showing:
10—screw rotation wheel,
11—delivery system,
12—lock button,
17—screw,
18—slider,
20—cam,
22—moveable clip,
25—rubber coupling,
26—delivery system through hole in the slider;
35—hollow tube;
FIG. 6 shows the assembled device with unlocked hoes, wherein:
18—slider,
19—spherical member,
20—cam,
21—spring wedge,
22—moveable clip,
23—cone-shaped wedge member,
24—lateral wedge member,
25—rubber coupling,
26—delivery system through hole in the slider;
FIG. 6a shows the assembled device with locked hoes, wherein:
18—slider,
19—spherical member,
20—cam,
21—spring wedge,
22—moveable clip,
23—cone-shaped wedge member,
24—lateral wedge member,
25—rubber coupling,
26—delivery system through hole in the slider;
FIG. 7 shows the unassembled device, wherein:
13—lateral wedge member rounded side
14—spring slider track,
18—slider,
19—spherical member,
20—cam,
21—spring wedge,
22—moveable clip,
23—cone-shaped wedge member,
24—lateral wedge member,
25—rubber coupling,
26—delivery system through hole in the slider,
30—cone-shaped wedge member cone,
31—delivery system hole in the cone-shaped wedge member,
32—slider hole for accommodating the wedge,
34—delivery system hole in the lateral wedge member;
FIG. 7a is a general view of a slider with a wedge, showing:
13—rounded portion of the lateral wedge member
18—slider,
19—spherical member,
21—spring wedge,
30—cone-shaped member cone,
31—delivery system hole;
FIG. 7b is a general view of a wedge, showing:
13—rounded side of the lateral wedge member,
21—spring,
23—cone-shaped wedge member,
24—lateral wedge member,
30—cone-shaped member cone wedge,
31—delivery system hole in the cone-shaped wedge member,
FIG. 8 is a top view of the device according to an embodiment using a moveable tail portion, showing:
1—device body,
27—retractable tail portion,
28—lock,
29—lock cutout in the lateral body portion;
FIG. 8a is a side view of the device according to an embodiment using a moveable tail portion, showing:
1—device body,
27—retractable tail portion,
28—lock,
29—lock cutout in the lateral body portion;
FIG. 9 is a general view of the device according to an embodiment using a moveable tail portion, showing a locked tail portion, wherein:
10—screw rotation wheel,
27—retractable tail portion,
28—lock,
29—lock cutout in the lateral body portion;
FIG. 10 is a general view of the device according to an embodiment using a moveable tail portion, showing an unlocked tail portion, wherein:
10—screw rotation wheel,
27—retractable tail portion,
28—lock,
29—lock cutout in the lateral body portion;
FIG. 11 is a general view of the device according to an embodiment using a moveable tail portion, showing a half-unlocked tail portion, wherein:
10—screw rotation wheel,
27—retractable tail portion,
28—lock,
29—lock cutout in the lateral body portion.

Below is provided the description of the invention with reference to the attached drawings.

The device comprises a body 1 (FIG. 1) made by casting of medical-grade plastic provided with a moisture-resistant coating 6 (FIG. 1) where it contacts the operator's hand, wherein the body's left and right halves (FIG. 1) are separately formed by casting and joined together after a screw 17 (FIG. 5) is accommodated therein with a screw rotation wheel 10 (FIG. 1, FIG. 5), a slider 18 (FIGS. 5, 6) provided with a spherical member 19 (FIGS. 6, 6a), a cam 20 (FIGS. 5, 6, 6a), moveable clips, 22 (FIGS. 5, 6, 6a) with a rubber coupling 25 (FIGS. 6, 6a), a wedge with a cone-shape wedge member 23 (FIGS. 6, 6a, 7) and a lateral wedge member 24 (FIGS. 6, 6a, 7), and a wedge spring 21 (FIGS. 6, 6a, 7) accommodated in the slider 18 track 14.

The body is comprised of a front truncated body portion 3 (FIG. 1) with a through hole 9 (FIG. 1) provided therein for a delivery system 11 (FIG. 1) and a left hand finger recess 5 (FIG. 1), a rear rounded body portion 4 (FIG. 1) with a through hole 9a (FIG. 1) provided therein for the delivery system and a palm rest 8 (FIG. 1) in the form of a tail portion formed above said rear rounded body portion 4, and a cylindrical central body portion 2 (FIG. 1). In an upper body 1 portion (FIG. 1), a transparent window 7 is formed for a control bar with score marks (FIG. 1), and a lock button 12 (FIG. 1) is accommodated in a hole 15 (FIG. 1) provided in a left lateral body portion. An upper portion of the screw 17 (FIG. 5) rotation wheel 10 (FIG. 5) is accommodated between the front truncated body portion 3 and the cylindrical body portion 2 (FIG. 1).

The mechanism accommodated in the body 1 (FIG. 1) is comprised of the screw 17 (FIG. 5) having the screw rotation wheel 10 (FIG. 5) rigidly locked on its one side and protruding from the body 1 outer side (FIG. 1), and at the opposite side the slider 18 (FIG. 5, FIG. 7) with the spherical member 19 (FIGS. 6, 6a, 7) having the cam 20 moveably mounted thereon (FIGS. 5, 6, 6a, 7) with moveable rubber clips 22 (FIGS. 5, 6, 6a, 7) provided along its axis, said clips 22 pressed together by the rubber coupling 25 (FIGS. 5, 6, 6a, 7). In the lock button hole 15 on the inner body side (FIG. 1), there is accommodated an inner member of the lock button 12 with lateral stiffening ribs, said inner member being moveable both towards the wedge comprised of the cone-shape member 23 and the lateral member 24 (FIGS. 6, 6a) and away from the same for unlocking or locking the moveable clips 22 (FIGS. 5, 6, 6a) as a result of contraction and release of the rubber coupling 25 as the delivery system 11 is accommodated inside the device.

In the spherical member 19 (FIGS. 6, 6a) of the slider 18 (FIGS. 6, 6a), horizontal channel holes are provided for accommodating therein the delivery system 11 (FIG. 5).

To accommodate the delivery system 11 inside the device, the operator depresses the lock button 12 (FIGS. 1, 3) whose inner member exerts pressure on the rounded portion 13 (FIGS. 7, 7a, 7b) of the lateral wedge member 24 (FIG. 6) which pushes the cone-shaped wedge member 23 (FIG. 6) out towards the moveable hoes 22 (FIG. 6) and whose cone 30 (FIGS. 7a, 7b) causes the moveable clips (FIG. 6) pressed together by the rubber coupling 25 (FIG. 6) to unlock so that a free through hole emerges for accommodation of the delivery system 11 (FIG. 5) inside the device. The delivery system 11 (FIG. 5) is introduced into the device through the holes 9, 9a (FIG. 1) in the rounded rear body portion 4 (FIG. 1) and truncated front body portion 3 (FIG. 1). Then, the lock button 12 is released (FIG. 5), the spring 21 (FIG. 6a), accommodated in the slider 18 track 14 (FIG. 7) pushes the lateral member 24 out (FIG. 6a) and the cone-shaped member 23 (FIG. 6a) returns to its original position as the rubber coupling 25 (FIG. 6a) presses the clips 22 together (FIG. 6a).

The operator uses the screw rotation wheel 10 (FIG. 1) to translate the rotational movement of the screw rotation wheel 10 (FIG. 5) into the linear motion of the slider 18 (FIG. 5) and advances the delivery system 11 (FIG. 1) horizontally inside the device such that it may rotate around its own axis, controlling its advance using the transparent window 7 (FIGS. 1, 2) for the control bar with score marks. The device is configured such that the slider 18 (FIG. 5) advances by a few millimeters as the screw rotation wheel 10 (FIG. 5) takes one turn.

In an embodiment of the invention, the device may be used with the delivery system 11 (FIG. 5) pre-locked therein such that it is unnecessary to arrange in advance the delivery system inside the device.

In another embodiment of the invention, the stent may be placed on the delivery system in a safe manner using a hollow tube 35 arranged in advance inside the device such that the delivery system 11 (FIG. 5) with the stent is introduced into the tube 35 which is then removed from the device.

In an embodiment of the invention, the tail portion 27 of the body 1 may be moveable (FIGS. 8, 8a, 9, 10, 11) for controlling its position using the locks 28 (FIGS. 8, 8a, 9, 10, 11) provided in the body lateral cutouts 29 (FIGS. 8, 8a, 9, 10, 11).

The invention claimed is:

1. A device for positioning a coronary stent within a coronary artery, characterized in that it comprises a body with a screw rotation wheel whose upper portion projects over the body and the lower portion is arranged inside the body and is rigidly connected to having a horizontal screw having a slider arranged thereon slidably along the screw and a cam moveably arranged on a screw spherical member horizontally to the screw with clips provided on the axis of said cam, said clips being pressed together by a rubber coupling, said body having a truncated shape in its front portion and recesses adapted for being held by an operator's left hand, and a rear upper body portion arranged as a tail portion to provide a palm rest for the right hand, wherein a transparent rectangular window for a control bar is provided in the upper body portion and through holes are provided in the front and rear body portions for a delivery system with the coronary stent, a lock button is accommodated in the lateral body portion with its inner side arranged inside the body and comprising a rectangular plate centered by two lateral stiffening ribs arranged inside the body and enabling the plate to freely move into the body towards a wedge provided on the opposite side of the slider and comprised of a lateral wedge member and a cone-shaped wedge member with the lateral wedge member arranged within a lateral hole in the slider on the lock button side and formed by a cutoff at an angle of 45 degrees on one side and at an angle of 90 degrees on the other side opposite to the lock button, wherein on the side cut off at an angle of 45 degrees the lateral wedge member is arranged end-to-end to the cone-shaped wedge member whose lower end portion is respectively cut off at an angle of 45 degrees and the opposite upper portion comprises a cone projecting from the hole in the slider on the clips side and contacting the same, in the lateral and cone-shaped wedge members, holes are provided through which, when the clips arranged on the slider are unlocked, the coronary stent delivery system advances, a spring is secured to the slider wall on the side opposite to the lock button, said spring contacting, via the lateral through hole in the slider, the lateral wedge member end at the point of the 90° cutoff.

2. The device according to claim 1, characterized in that the body is made of medical-grade plastic provided with a moisture-resistant coating where it contacts the operator's hand.

3. The device according to claim 1, characterized in that the body tail portion is formed moveably along the body on lateral cutouts and is lockable by means of locks arranged on its sides in the front part thereof.

4. The device according to claim 1, characterized in that the delivery system with the stent is locked in advance therein.

5. The device according to claim 1, characterized in that a hollow tube is introduced in advance therein for accommodating the delivery system with the stent therein.

6. The device according to claim 1, characterized in that the device is provided using a worm gearing, toothed gearing and rope transmission.

7. A method for positioning a coronary stent within a coronary artery, characterized in that a coronary stent delivery system is placed in a device body by depressing a lock button arranged in a lateral body portion, wherein its inner side, arranged within the body and comprising a rectangular plate centered by two lateral stiffening ribs arranged within the body and enabling the plate to freely move into the body towards a wedge, exerts pressure on a rounded surface of the lateral wedge member arranged in a lateral through hole in slider on the lock button side and cooperates with the cone-shaped wedge member at the point of the 45° cutoff on one side for displacing a cone-shaped wedge member towards clips and with a spring arranged in the lateral through hole in the slider on the side opposite to the lock button at the point of the 90° cutoff of the slider, the cone-shaped wedge member releases the clips pressed together by a rubber coupling to form a through hole for accommodating the delivery system within the device, and when the lock button is no longer depressed, the lateral wedge member returns to its initial position to leave space for the cone-shaped member so that the clips contracts to lock the delivery system within the device, whereafter a screw rotation wheel is rotated for translating a rotational movement of the wheel into the linear motion of the slider with the locked delivery system to a required distance both back and forth inside a coronary vessel.

* * * * *